United States Patent
Smith et al.

(10) Patent No.: US 9,618,443 B2
(45) Date of Patent: Apr. 11, 2017

(54) GEMSTONE INSPECTION (71) Applicant: DE BEERS CENTENARY AG, Lucerne (CH)

(72) Inventors: James Gordon Charters Smith, Buckinghamshire (GB); Timothy Howard Leaton, Berkshire (GB)

(73) Assignee: De Beers UK Ltd., London (GB)

( * ) Notice: Subject to any disclaimer, the term of this patent is extended or adjusted under 35 U.S.C. 154(b) by 228 days.

(21) Appl. No.: 14/384,859

(22) PCT Filed: Mar. 13, 2013

(86) PCT No.: PCT/EP2013/055165
§ 371 (c)(1),
(2) Date: Sep. 12, 2014

(87) PCT Pub. No.: WO2013/135781
PCT Pub. Date: Sep. 19, 2013

(65) Prior Publication Data
US 2015/0015877 A1 Jan. 15, 2015

(30) Foreign Application Priority Data
Mar. 16, 2012 (GB) .................................. 1204680.1

(51) Int. Cl.
*G01N 21/00* (2006.01)
*G01N 21/13* (2006.01)
(Continued)

(52) U.S. Cl.
CPC ........... *G01N 21/13* (2013.01); *B07C 5/3425* (2013.01); *B07C 5/366* (2013.01); *B07C 5/38* (2013.01);
(Continued)

(58) Field of Classification Search
CPC .... G01N 21/13; G01N 21/87; G01N 21/8806; G01N 21/64; G01N 21/65; G01N 33/381; B07C 5/34
(Continued)

(56) References Cited

U.S. PATENT DOCUMENTS 2,690,258 A 9/1954 Cox
4,186,838 A 2/1980 Levitt et al.
(Continued)

FOREIGN PATENT DOCUMENTS

CN 201637679 U 11/2010
GB 941 301 A 11/1963
(Continued)

OTHER PUBLICATIONS

Australian Search report for corresponding Australian Application No. 2013231242 dated Feb. 23, 2016.
(Continued)

*Primary Examiner* — Abdullahi Nur
(74) *Attorney, Agent, or Firm* — Renner, Otto, Boisselle & Sklar, LLP (57) ABSTRACT

There is described an apparatus and method for inspecting and optionally sorting gemstones. The apparatus includes a nozzle or array of nozzles operatively connected to a vacuum pump such that a gemstone located generally underneath one of the nozzles will be supported against that nozzle by air pressure when a vacuum is applied above the nozzle. A drive system moves the nozzles along a path past a gemstone pick-up location so that a gemstone can be picked up by each nozzle as that nozzle passes the pick-up location. One or more measurement devices are located on or near the predetermined path and configured to measure at least one property of the gemstone. One or more ejection locations are provided on the path at which the vacuum
(Continued)

applied to each nozzle is reversible to eject the gemstone from that nozzle. The apparatus may also include a plurality of dispensing bins into which the gemstones are dispensed. The bin into which each gemstone is dispensed is chosen in dependence on the measured property.

27 Claims, 6 Drawing Sheets

(51) Int. Cl.
  *B07C 5/342* (2006.01)
  *B07C 5/36* (2006.01)
  *B07C 5/38* (2006.01)
  *G01N 21/87* (2006.01)
  *G01N 21/25* (2006.01)
  *G01N 21/31* (2006.01)
  *G01N 33/24* (2006.01)

(52) U.S. Cl.
  CPC .............. *G01N 21/25* (2013.01); *G01N 21/31* (2013.01); *G01N 21/87* (2013.01); *G01N 33/24* (2013.01); *G01N 2021/135* (2013.01)

(58) Field of Classification Search
  USPC .......................................................... 356/30
  See application file for complete search history.

(56) References Cited

U.S. PATENT DOCUMENTS

| | | | |
|---|---|---|---|
| 4,379,510 A | 4/1983 | Ziegel | |
| 4,414,566 A * | 11/1983 | Peyton | B07C 5/10 198/340 |
| 4,793,707 A | 12/1988 | Hata et al. | |
| 7,105,822 B1 | 9/2006 | Beesley | |
| 2004/0194639 A1 | 10/2004 | Ilch et al. | |
| 2005/0262712 A1* | 12/2005 | Green | B43L 23/00 30/451 |
| 2008/0200108 A1* | 8/2008 | Kupferberg | F23L 17/02 454/40 |

FOREIGN PATENT DOCUMENTS

| | | |
|---|---|---|
| GB | 1 231 704 A | 5/1971 |
| GB | 1 528 699 A | 10/1978 |
| GB | 2 110 416 A | 6/1983 |
| GB | 2 273 154 A | 6/1994 |
| JP | 09-029186 | 2/1997 |
| JP | 10-148616 A | 6/1998 |
| WO | WO 87/01974 A1 | 4/1987 |
| WO | WO 87/01975 A1 | 4/1987 |
| WO | WO 99/61890 A1 | 12/1999 |
| WO | WO 2009/133393 A1 | 11/2009 |
| WO | WO 2011/054822 A1 | 5/2011 |

OTHER PUBLICATIONS

International Search report for corresponding International Application No. PCT/EP2013/055165 mailed Mar. 4, 2014.
British Search report for corresponding British Application No. GB1204680.1 dated Jun. 28, 2012.

* cited by examiner

GEMSTONE INSPECTION

TECHNICAL FIELD

The present invention relates to a system for inspecting gemstones. In particular, although not exclusively, the invention relates to a system for inspecting and sorting gemstones such as diamonds.

BACKGROUND

As used herein, the term "gemstone" is intended to cover cut stones, or rough stones which may in future be cut.

Diamonds can be graded according to characteristics such as colour and clarity. The grading of a diamond may be used in determining its value for applications such as jewellery making. In general, the market value of a polished diamond depends on its colour, cut proportions, internal clarity and weight, known as the "Four Cs".

Grading is generally carried out by trained professionals who view diamonds under ten times magnification. Such professionals may grade a diamond by observing its colour, and by looking for blemishes on the diamond's surface and inclusions within the diamond in order to determine its clarity. Some subjectivity is inevitable when grading is carried out by human beings, and it would be desirable to be able to sort rough or polished diamonds objectively. Furthermore, it is desirable to process large numbers of stones quickly, and this is not possible if each must be examined by a human being. Similar issues arise for other gemstones.

It would therefore be desirable to provide a system to inspect gemstones such as rough diamonds in a reliable and repeatable manner. Such an inspection system may then be employed in a sorting machine where the result of an inspection determines into which category the gemstone is sorted, and supplies means to allow it to be placed into a bin, container or the like. But equally it may be used to inspect a group or parcel of diamonds and forming a characterisation or valuation of said diamond parcel without separating them. The invention may also be applied to the inspection of industrial or synthetic diamond material.

At a basic level this inspection may determine whether the object really is a diamond, perhaps using Raman scattering, but more sophisticated distinctions may be drawn based on colour, clarity, shape or other physical properties, for example.

Regardless of the application, the prior art contains numerous examples of machines designed to inspect diamonds, often in high volumes, for example at a rate of up to 15 per second. Other examples have a much lower throughput, in one extreme taking up to 5 minutes to inspect one stone. Where the throughput is low it may be practical to load the machine by hand so that the technical task of presenting the stone to the measurement device or devices is carried out by hand (often using tweezers) but for larger volumes the task of delivering and removing the gemstone from the inspection device needs to be automated if efficient production is to be carried out.

Many prior art systems employ a container such as a roller hopper which may in the simplest case drop the stone directly into the measurement device, or alternatively into a second transporter such as a vibratory track or feeder which drops a stream of diamonds or other gemstones from a single point (i.e. the end of the feeder). The advantage of the latter scheme is that there is better control of the trajectory of the diamond because its release point is known, but there are still uncertainties in the trajectory at a later time because its launch velocity is not fully controlled and there is no control over when stones are released.

These issues present significant challenges to the designer of the measurement device because it has to cope with stones arriving at random times and over a larger range of locations than is strictly necessary. This lack of precision results in a measurement device which copes with the variation either by increased complexity or by having a compromised performance.

For example, it is well known that diffraction causes the resolution of an optical system to be compromised if it is to provide a large depth of focus. There is an underlying minimum depth of focus that may be required in order to have the entire object in focus, but if there is an additional uncertainty in position caused by the delivery system the designer of the optical system must compromise the resolution to accommodate it.

The problems are further compounded when observations from a plurality of viewpoints relative to the object are required for the measurement. A plurality of measurement devices need to be concentrated around a nominal point in space where the measurement is to take place and they may well interfere with each other. In principle the devices could be separated approximately vertically along the nominal trajectory but as the object falls uncertainties in time and position increase leading to further technical problems.

SUMMARY

The present invention is intended to mitigate or reduce at least some of these limitations, thus improving the accuracy and/or reliability or reducing the cost of automated inspection.

In accordance with one aspect of the present invention there is provided an apparatus for inspecting gemstones. The apparatus comprises a vacuum nozzle for picking up a gemstone from a supply of gemstones and a transport mechanism for transporting the nozzle and associated gemstone to one or more measurement locations. A measurement system comprising one or more measurement devices, configured to measure one or more properties of the gemstone, is located proximate to the one or more measurement locations. A control system is operatively coupled to the vacuum nozzle and measurement system and configured so that the gemstone arrives at the or each measurement location at a time known by the measurement system. A positive pressure application system is provided for releasing the gemstone from the nozzle at an ejection location.

Thus any individual stone can be tracked, and measurements can be carried out in a controlled environment at a predictable time, reducing the overheads required by the measuring devices. The apparatus can be used to inspect either rough or cut gemstones.

At least one of the one or more measurement devices may be located proximate to at least one of the one or more measurement locations in such a way as to measure at least one of the one or more properties of the gemstone while the gemstone is held on the nozzle. The gemstone may be conveyed on the nozzle to a plurality of measuring devices in sequence, each receiving the object at controlled times and locations.

The apparatus may further comprising nozzle manipulation means for changing the orientation of the gemstone as it travels between the measuring devices, optionally by rotating the nozzle about its own axis. At least some of the measuring devices may be substantially identical so as to measure the same property of the gemstone at different orientations.

Alternatively, each measuring device may conduct a different measurement, although some or all of these measurements may be complementary to one another.

Instead of, or as well as, measurement on he nozzle, the apparatus may be configured to conduct measurements following release from the nozzle. In this case the ejection location may be coincident with one of the one or more measurement locations such that, following release from the nozzle, the gemstone falls along a predetermined path through the one or more measurement devices within a specified time window.

The one or more properties may include optical properties.

The apparatus may also comprise a plurality of dispensing bins into which the gemstones can be dispensed, the bin into which each gemstone is dispensed being chosen in dependence on the one or more measured properties. A plurality of ejection locations may be provided, each ejection location being associated with a delivery mechanism to one of the dispensing bins, the ejection location at which the positive pressure is applied for any given nozzle being chosen in dependence on the one or more measured properties of the stone held by that nozzle.

Alternatively or in addition, a rotatable carousel may be provided. The carousel may comprise a plurality of socks and have at least a portion located beneath one of the one or more ejection locations so that a gemstone ejected at that ejection location falls into one of socks. The carousel may also include a plurality of selectively actuable release points for releasing the gemstone from the socks, each release point associated with a delivery mechanism to one of the dispensing bins. The apparatus may then be configured so that the activation of a release point is chosen in dependence on the measured properties of a stone carried by the sock passing through that release point.

The carousel may be configured to rotate such that the sock passing under the ejection location is moving at substantially the same speed and in the same direction as the nozzle moving through the ejection location. A double feed detector may be provided for identifying if two or more stones are ejected at the ejection location into a single sock.

One of the measurement devices may comprise a collimated light source and a viewing means arranged so that a gemstone on a nozzle passes between the light source and the viewing means, so as to obtain a series of silhouette images of each gemstone. The apparatus may then also include processing means for constructing a 3D model of the shape of each gemstone from the series of images.

One of the measurement devices may comprise a spectrometer for determining an absorption and/or photoluminescence spectrum of a gemstone passing that measurement device.

One or more of the measurement devices may include a diffuse light source and an array of cameras at different locations and a means for rotating the nozzles between the different locations the viewing means coupled to a processing means for identifying a colour of the gemstone when illuminated by the light source.

One of the measurement devices may include a diffuse light source and a camera located below the predetermined path for obtaining an image of each gemstone from beneath. The or each nozzle may comprise a transparent wall surrounding a bore for supplying a vacuum to an opening of the nozzle, an obstruction in the bore obstructing a line of sight from the opening into the bore, the partial obstruction including a diffuse reflecting surface on a side facing the opening, and a support structure for holding the obstruction in place in such a way as to allow airflow around the obstruction.

The at least one nozzle may comprise a wall surrounding a bore for supplying a vacuum to an opening of the nozzle, and the at least one measurement device may be arranged to measure at least one optical property of the gemstone through the bore.

The at least one nozzle may further comprise at least one optical fibre within the bore and may be configured to allow airflow around the optical fibre.

The at least one measurement device may be synchronously movable with the at least one nozzle and arranged to allow measurement of the at least one optical property of the gemstone through the bore at any time during the transport of the nozzle and gemstone.

The at least one measurement device may be fixed with respect to the transport mechanism, and may be arranged to measure the at least one optical property of the gemstone through the bore as the gemstone passes a corresponding measurement location.

The transport mechanism may be a rotatable hub around which is disposed an array of nozzles. The hub may include a series of apertures, each communicating with one of the nozzles, into which a jet of fluid is introducible in order to provide the application of positive pressure at that nozzle at the ejection location. The hub may also have the ability to move in the direction of the axis of the nozzles to facilitate different stone sizes.

A bowl may be provided for presenting the gemstones to the array of nozzles, the bowl rotatable at a rate chosen such that stones will move past a pick-up location in the same direction as the nozzle passing the pick-up location. The bowl may be laterally offset from the nozzle array, and configured to rotate in an opposite direction to the hub.

A cam surface may be located above the pick-up location, and each nozzle may be located on a mount configured to follow the cam surface and move the nozzle closer to the bowl as that nozzle passes the pick-up location. Alternatively, the nozzle array may be configured to rotate around an axis at an angle compared to an axis of rotation of the bowl so that the nozzles approach the bowl as they approach the pick-up location.

A controlled feed mechanism may feed stones into the bowl at a predetermined rate.

In accordance with another aspect of the present invention there is provided a method for sorting gemstones. The method comprises picking up gemstones individually from a supply of gemstones using a moving nozzle or array of nozzles under vacuum. One or more measurements are performed on each gemstone while mounted on its associated nozzle to identify at least one property of that gemstone. Each gemstone is released into a bin selected from a plurality of bins in dependence on the measured property of that gemstone.

In accordance with a further aspect of the present invention there is provided a method for inspecting gemstones. The method comprises picking up gemstones individually from a supply of gemstones using a moving nozzle or array of nozzles under vacuum. The gemstone is released at an ejection location so that it passes in freefall through a measurement cell. At least one property of the gemstone is measured in freefall through the measurement cell. Each gemstone may be directed into a bin selected from a plurality of bins in dependence on the measured property of that gemstone.

The step of releasing a gemstone into the selected bin may include dropping the gemstone into a sock in a rotating carousel of socks, and releasing the gemstone from the sock at a location determined by the measured properties of the gemstone.

In accordance with another aspect of the present invention there is provided a nozzle for supporting a gemstone. The nozzle comprises a wall surrounding a bore for supplying a vacuum to an opening of the nozzle, the wall being formed from a clear material. An obstruction is located in the bore obstructing a line of sight from the opening into the bore, the obstruction including a diffuse reflecting surface on a side facing the opening. A support structure holds the obstruction in place in such a way as to allow airflow around the obstruction.

In accordance with another aspect of the present invention there is provided a nozzle for supporting a gemstone. The nozzle comprises a central bore for supplying a vacuum to a plurality of apertures formed through a generally flat support face at the end of the nozzle against which a flat face of the gemstone can be held. The nozzles may be of varying lengths to allow analysis of a range of stone sizes.

In a one embodiment a gemstone is picked up automatically by a vacuum nozzle from a supply of gemstones and is released from the end of the nozzle by application of positive pressure at a predetermined location and at a time known to the measurement system in proximate vicinity to one or more measurement devices so that it drops along a well controlled path within a specified time window through the measurement devices.

In another embodiment a gemstone is picked up by a vacuum nozzle and is conveyed to at least a first measurement location while still on the nozzle, so that the position and time of arrival is under control. The gemstone may be conveyed on the nozzle to a plurality of measuring devices in sequence, each receiving the object at controlled times and locations, each device performing different but possibly complementary measurements In a further embodiment the gemstone is conveyed to a first measurement location while on a vacuum nozzle and a series of distinct observations are made, wherein the orientation of the gemstone is changed by manipulation of the nozzle, for example by rotating the nozzle about its own axis.

In another embodiment the gemstone is conveyed to plurality of measurement devices in sequence, each device measuring essentially identical properties, wherein the orientation of the gemstone is changed by manipulation of the nozzle, for example by rotating the nozzle about its own axis so as to produce a series of distinct observations.

It will be appreciated that any of the above schemes may be combined.

Furthermore, any of the above schemes may be carried out with a vacuum nozzle whose physical properties are designed to have negligible effect on the result of the measurement. In particular for an optical measurement a substantially transparent nozzle is employed which contains a diffusely reflecting baffle so as to block a direct line of sight from the optical inspection means through the gemstone up the bore of the vacuum nozzle.

BRIEF DESCRIPTION OF THE DRAWINGS

Some preferred embodiments will now be described by way of example only and with reference to the accompanying drawings, in which.

DETAILED DESCRIPTION

Figure 1:
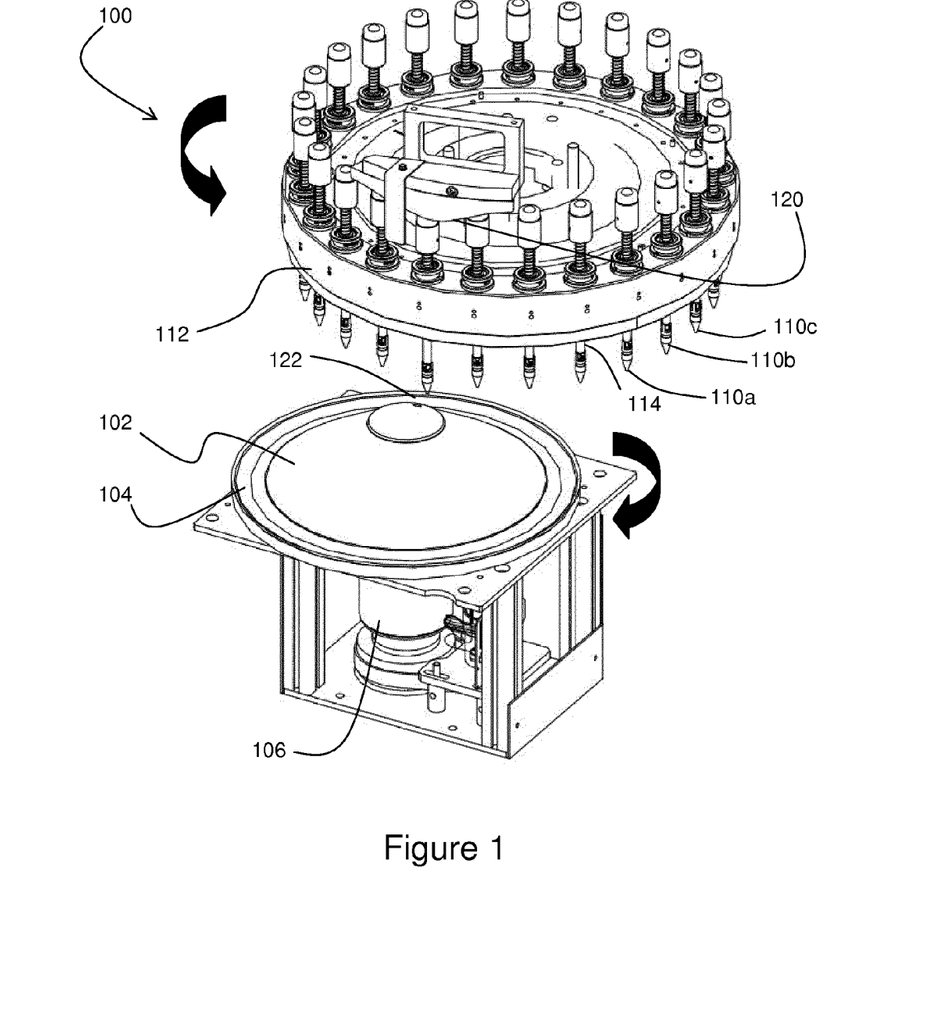
FIG. 1 is a schematic illustration of an apparatus for transporting individual objects to a measurement location.
Figure 2:
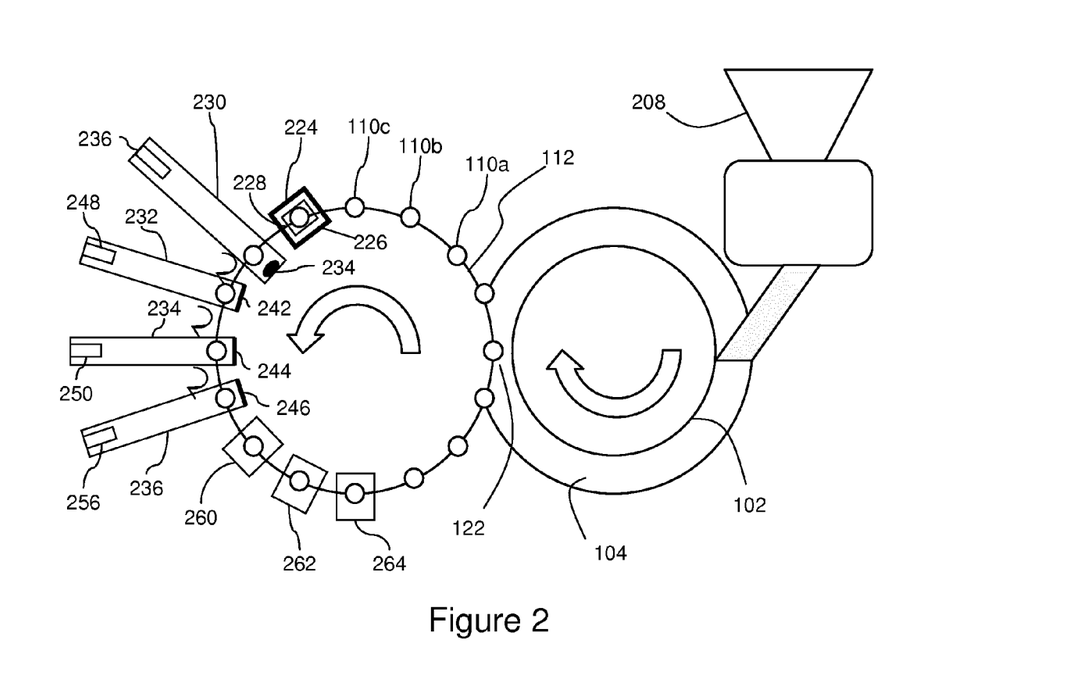
FIG. 2 is a schematic top view of the apparatus of FIG. 1.

FIG. 1 is an illustration of an apparatus 100 for transporting individual objects to a measurement location. In the following discussion the apparatus will be described in the context of transporting gemstones such as diamonds, but it will be appreciated that the apparatus may be used to transport other small objects. FIG. 2 is a schematic top view of selected parts of the apparatus 100.

The apparatus 100 comprises a generally circular feeder bowl 102 which has a trough 104 around its peripheral edge. A motor 106 located underneath the feeder bowl rotates the bowl.

A flow of stones is fed into the trough 104 as it rotates. The stones may be loaded into a hopper 208 (not shown in FIG. 1) and fed through a pair of resilient co-operating rollers to ensure an even flow. Feeders of this type are described, for example, in GB 2162828, GB 2194518 or GB 2194779, although it will be appreciated that any suitable feeder may be employed.

A circular array of nozzles 110a, 110b . . . is supported by a feeder hub 112 above and laterally offset from the bowl 102 so that the array and trough 104 overlap each other, as is apparent from FIG. 2. The feeder hub 112 is powered so as to rotate in the opposite direction to the bowl 102, so that where the nozzles pass over the trough they are moving in the same direction as the trough. Perfect speed matching is not required. In FIG. 2 the feeder hub 112 and bowl 102 are shown as being the same size, and will therefore rotate at the same rate, but it will be appreciated that the feeder hub 112 and bowl can be different sizes, as long as the relative rotation rates are adjusted accordingly.

Each nozzle 110a, 110b . . . is mounted on the feeder hub via a longitudinal mount 114 which extends generally vertically. Each mount 114 is vertically moveable relative to the feeder hub 112, and is constrained and sprung 116 so as to be maintained at the highest point of that constraint in normal use. Each mount 114 is also provided with a cam follower 118 at its top end.

A cam surface 120 is located above the nozzle array at the point at which the array and the trough 104 overlap. As each nozzle passes under the cam surface 120, the cam follower 118 contacts the surface and the mount 114 is pushed downwards towards the trough 104 so that the nozzle 110a, 110b . . . is in close proximity to the trough 104 at the same time as the two move at the same speed along a generally parallel course.

As the bowl 102 rotates, the stones are transported to a pick-up point 122 corresponding to the overlap between the trough. A vacuum is applied to the nozzles via an evacuation system (not shown). As each nozzle passes over the pick-up point 122, it is forced downwards on its mount 114 by the cam surface 120 so that it is moving just above and in approximately the same direction as the layer of stones in the trough 104. One of the stones is therefore picked up by that nozzle 110a, 110b, 110c . . . .

As the feeder hub rotates, the stones mounted on the nozzles pass through one or more measurement cells 224, 230, 232, 234, 236 shown schematically in FIG. 2 but not shown in FIG. 1. The measurement cells may be configured to measure a number of different properties of the stone, including for example the colour, shape or clarity of the stone.

The first measurement cell 224 enables an assessment of the optical properties of the stone to be carried. Diffuse light is emitted from the walls 226 of the cell to illuminate the stone from all directions. A camera 228 is located at the bottom of the cell so that it is underneath the stone as it passes through the cell 224. The camera records an image of the stone which can be analysed to provide a measure of the optical properties such as colour, and the presence of defects or inclusions in the stone.

In order to obtain additional colour information, one of the measurement cells 230 may be provided with an illumination means 238 configured to diffuse light towards the stone on the nozzle. A camera 240 is located in the cell to record an image of the light transmitted through the stone. The image can be analysed by a processor (not shown) to identify the colour of the stone. Alternatively, a spectrometer may be provided in the measurement cell to determine the transmitted wavelength(s) directly. A similar arrangement may be used to obtain full infra-red, ultra-violet and/or visible absorption spectra for the stone. Alternatively any other method to excite the stone via x-ray, infra-red, ultra-violet, laser and or visible light with an appropriate method of detection may be used to analyse the stone.

Other measurement cells 232, 234, 236 may be used to identify the colour of a stone. Each cell includes a diffuse illumination means 242, 244, 246 to illuminate the stone as it passes through the cell, and a camera 248, 250, 252 to record a colour image of the stone in that cell. A cam or other suitable arrangement (not shown) is mounted on or near the feeder hub and configured to rotate the mounts 114, and thus nozzles 110 with stones attached, about their own axes, between each cell 232, 234, 236, as shown in FIG. 2. A series of colour images of each stone are thus recorded at a variety of orientations of the stone, from which the colour of the stone can be calculated. It will be appreciated that cells 242, 244, 246 may effectively be combined so that a single diffuse light source is used to illuminate the stone in a plurality of different locations, with an array of cameras behind these locations. It is not required that there is a direct correlation between the number of light sources and the number of cameras, and it is not necessary to include separate "cells" to achieve this.

Further measurements may also be made in additional measurement cells (not shown). For example, measurement cells can be configured to measure other properties of the gemstones, such as clarity, size, and absorption characteristics such as infra-red or uv-vis absorption spectra. It is also possible to include a Raman spectrometer in order to identify the material of a gemstone—for example whether or not it is a diamond. It is also possible to measure the percentage yield of cut gemstones that could be cut from a given rough stone, or even the size and value of resulting gemstones, if enough data is gathered on the rough stone. Another possibility is that no measurement is made and the device is used to sample a small percentage of the stones. In another alternative, some measurement is made and the sample is guided by the measurement to provide a "stratified" sample.

As the feeder head continues to rotate, each stone moves over a series of dispense points located above chutes 260, 262, 264, each of which provides a route into a segregated bin. The properties of each stone, as identified by its passage through the measurement cells 330, determines the bin it should be dispensed into. One of the chutes 260, 262, 264 is therefore selected as the appropriate dispense point for that stone.

As the stone passes over the selected dispense point, the vacuum supplied to the nozzle is reversed so that the stone is blown off the nozzle and into the correct chute 260, 262, 264. Each mount includes a "blow-off hole" (not shown in FIG. 1) located in the above the nozzle so that a jet of air can be injected into that nozzle. The evacuation system can therefore provide a continuous "vacuum" to all of the nozzles which is selectively overridden for individual nozzles at the selected dispense points by injecting air into those nozzles when required.

For example, if the gemstones are being sorted by colour, each of the chutes 260, 262, 264 may be assigned to a different colour. The colour of each stone is identified as it passes through the colour measurement cell 230, and the appropriate bin selected on the basis of the measured colour.

It will be noted that the position of any given stone can be correlated to the vacuum nozzle which has picked it up from the trough 104. The stones are mixed and indistinguishable when they are in the bowl 102, but as soon as one has been picked up by a nozzle, the progress of that stone through the measurement cells can be tracked, and the various measurements obtained in the cells 224, 230, 232, 234, 236 can be associated with that stone. Thus a full picture of the optical properties (and/or shape or size) of that stone can be obtained before a decision is made as to the bin to which it should be dispensed.

As an alternative (or in addition) to direct dispensing of the stones into a range of bins, the apparatus may be provided with a carousel for dispensing the stones into a larger number of bins. This can be understood with reference to FIG. 3, which is a schematic top view of the apparatus of FIGS. 1 and 2 with an additional carousel 300 located under one of the dispense chutes 264.

Figure 3:
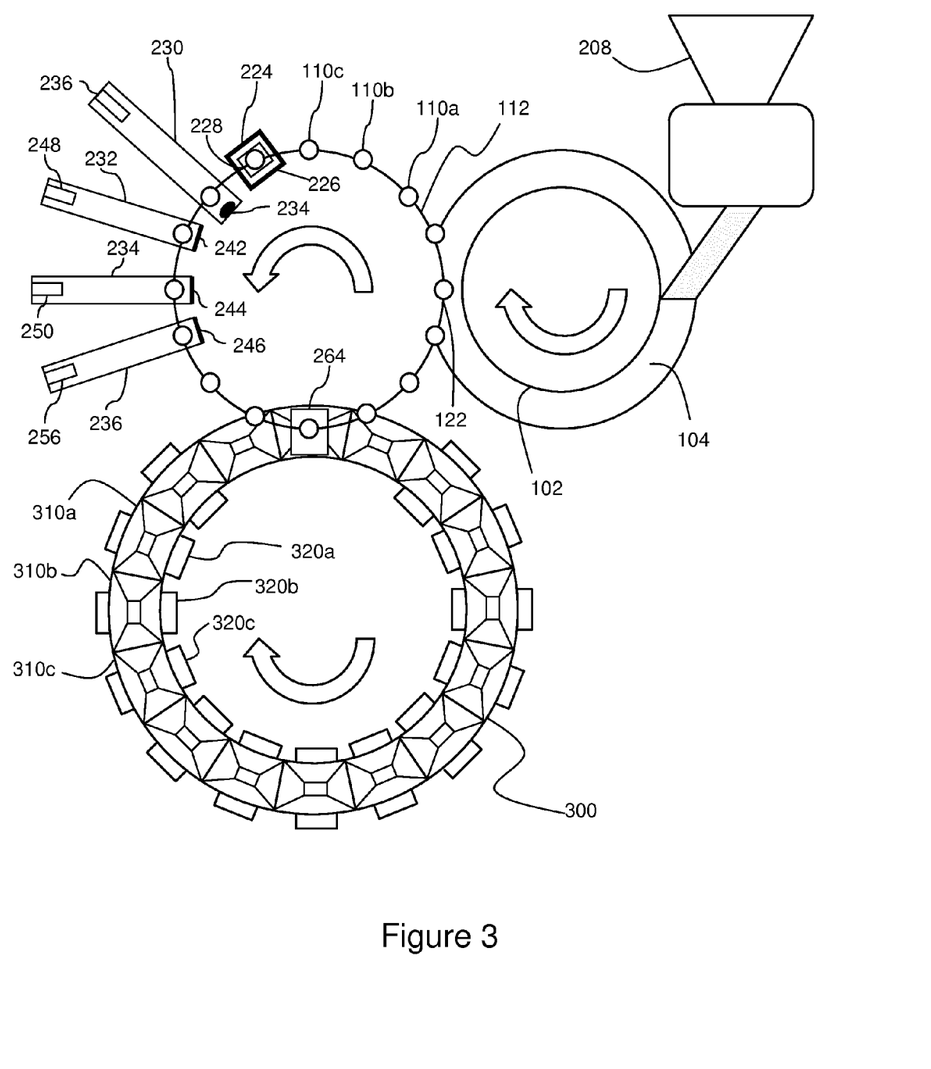
FIG. 3 is a schematic top view of an alternative arrangement of the apparatus of FIG. 1.

The carousel 300 rotates in the opposite direction to the feed hub 112 and includes an array of dispenser socks 310a, 310b, 310c . . . into which the stones can fall. Every time a nozzle with a stone attached passes over the dispense chute 264, the vacuum in that nozzle is reversed and the stone is blown off and into the dispense chute 264, falling into whichever dispenser sock happens to be underneath at the time. The system keeps track of which stones fall into which socks, because the relative locations of the containers 310a, 310b . . . of the carousel and the nozzles 110a, 110b . . . on the feed hub are also known.

Underneath the carousel is an array of chutes 320a, 320b, 320c . . . leading to discrete bins. A suitable bin is selected for each stone based on a chosen property such as colour, and when the sock in which that stone is located passes over the chute leading to the selected bin, a solenoid is activated to open the base of the sock and dispense the stone contained therein into the chute.

An advantage of this mechanism is that it maximises both the number of bins and the number of measurement cells available. Since only one dispense point needs 264 to be provided, there is space for a large number of measurement cells on the feeder hub. The carousel itself provides access to a large number of bins. The relative rates of rotation of the feeder hub 112 and carousel 300 are known, and this ensures that the location of each individual stone is known when it is held on one of the nozzles 110a, 110b . . . and subsequently when it is located in one of the socks 310a, 310b, 310c . . . . This ensures that the correct chute can be selected for each stone.

It will be appreciated that a combination of the two embodiments described above may also be employed: it is possible to include more than one dispense chutes 260, 262, 264 below the nozzle array, where one leads to a carousel 300 and the other(s) lead directly to bins.

In a further refinement, the chute 264 leading to the carousel may pass through a double feed detector, configured to identify if two stones are dropped through the chute. Suitable multiple feed detectors include multi-axis beam detectors are described, for example, in GB 2178547 and GB 2184832. This may occur, for example, if two stones are picked up on a single nozzle. In this eventuality, the bin selected from the carousel is a "recycle" bin from which the stones are returned to the bowl 102. This may not be necessary if some of the measurement cells 232, 234, 236 can detect from the shape of the object on any given nozzle that two stones are present.

Alternatively or in addition, the dispense chute may include a further measurement cell (not shown) through which the stones fall following blow-off from the nozzle. This measurement cell may include a light source and one or more cameras for identifying further properties of the stone as it falls between the light source and the camera(s). Examples of such free flight measurement are described in GB 2184832. This additional measurement may be taken into account in the decision as to which bin the stone is ultimately dispensed into.

Various configurations of the components described above may be envisaged. In one example the apparatus may be configured to reject stones having optical properties (for example clarity) which are below a predetermined threshold. Those stones which are above this threshold may then be measured and sorted based on a second criteria.

Figure 4:
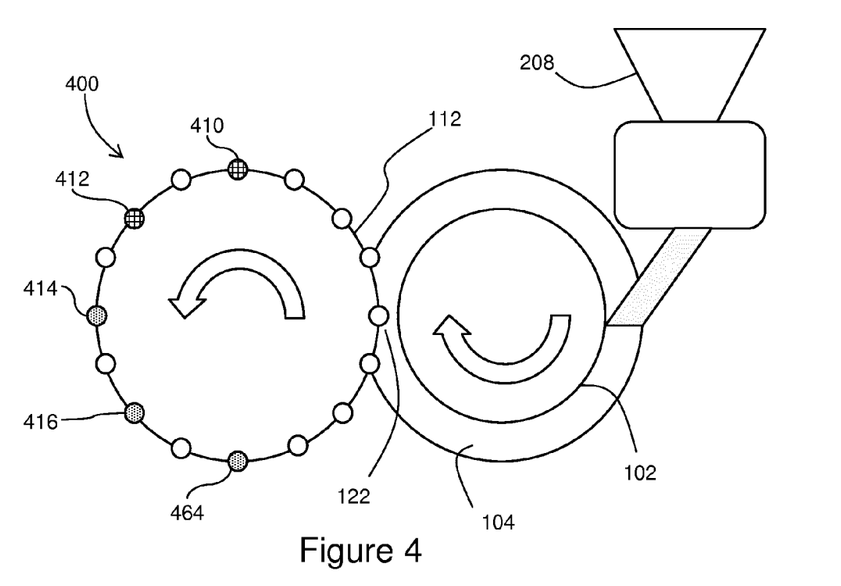
FIG. 4 is a schematic top view of an apparatus similar to that of FIG. 1 having different ejection points.

This can be understood with reference to FIG. 4, which is a schematic top view of parts of an apparatus 400 very similar to that of FIGS. 1-3. In this diagram measurement cells are not shown explicitly, but the points at which events occur are illustrated. In this example, threshold colour and clarity measurements are made "on nozzle" at two points 410, 412. If a stone falls below the colour threshold (for example it has more than a predetermined amount of brown in the spectrum) then at a first eject point 414 it is blown off the nozzle and into a first "reject" bin. If it passes the first test but falls below the clarity threshold then it is blown off the nozzle at a second eject point 416 into a second "reject" bin. If the stone passes both of the initial tests, it is blown off at a "measure and dispense" point 464, and falls through a measurement cell into a sock in a carousel below (not shown in FIG. 4).

Figure 5:
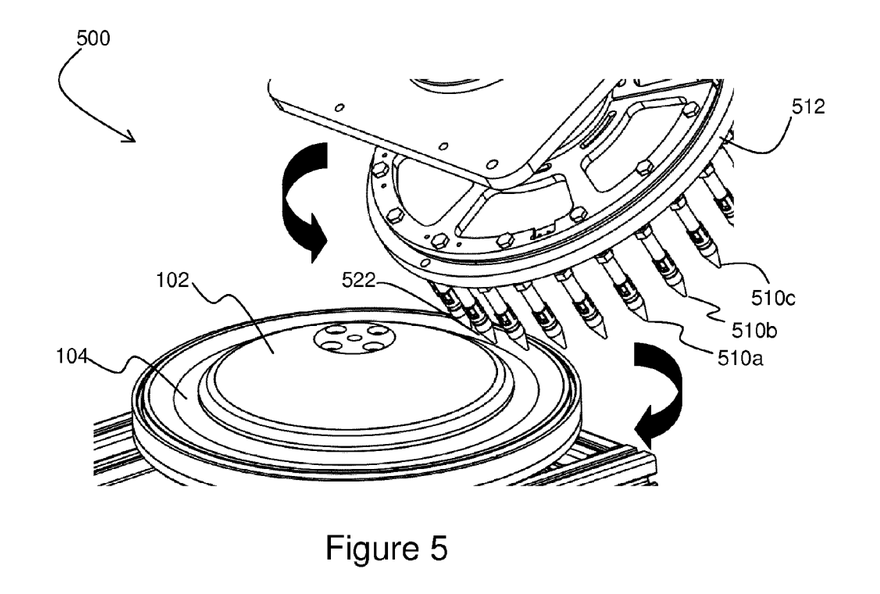
FIG. 5 is a schematic illustration of an alternative arrangement of a nozzle array.

FIG. 5 illustrates an alternative arrangement of an apparatus compared to that shown in FIG. 1. In the arrangement of FIG. 5, the feeder hub 512 is arranged at an angle to the bowl 102 so that the nozzles 510a, 510b, 510c . . . approach the trough 104 at the point 522 at which the bowl 102 and feeder hub 512 overlap. This does away with the need for a cam surface and vertically movable mounts. The arrangement of measurement cells and ejection points into chutes and/or a carousel located beneath the feeder hub are unchanged.

Figure 6:
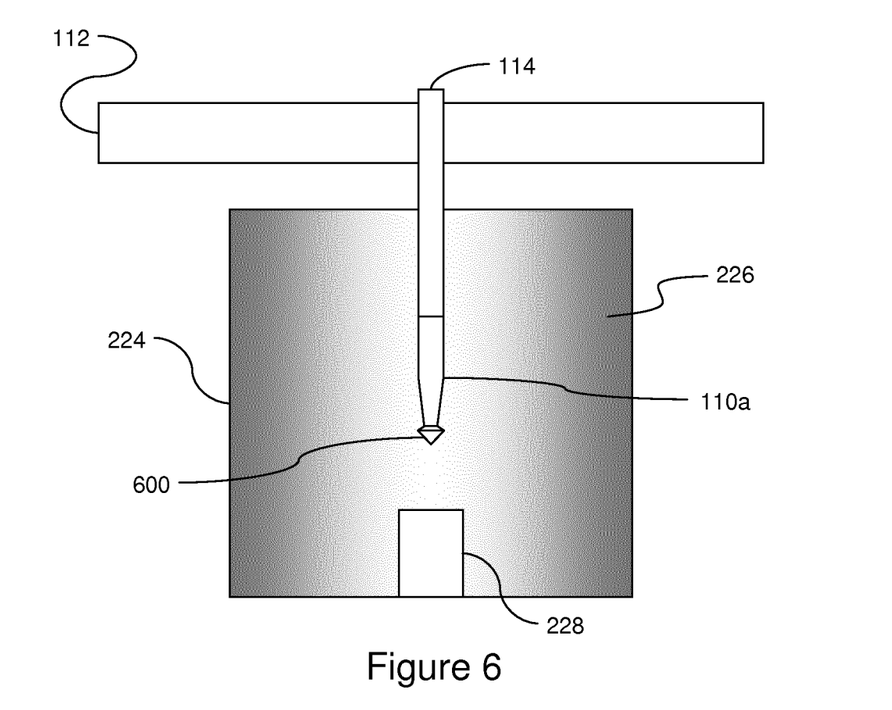
FIG. 6 is a schematic illustration of a measurement cell.

FIG. 6 is a schematic illustration of a measurement cell 224 configured to obtain an image of a stone 600 passing therethrough attached to a nozzle 110a. The cell includes a diffuse light source 226 arranged around the edges of the cell 224 so as to illuminate the stone from all directions. The diffuse light source may include a diffuser located in front of individual light sources, or may include a reflective material arranged around the walls of the cell and another light source (not shown) directing light into the cell. It will be appreciated that the cell is shown as being rectangular for convenience, but any suitable shape may be envisaged. In particular, it is likely that a cell of this type may be cylindrical. A camera 228 is located on the base of the cell and directed upwards, so that it can obtain an image of the gemstone as it passes overhead when illuminated from all directions.

Figure 7:
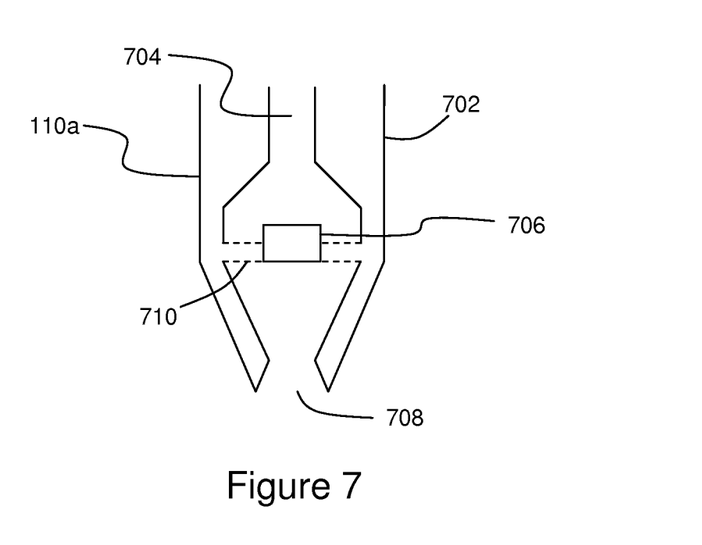
FIG. 7 is a schematic cross section through a nozzle.

FIG. 7 is a detailed schematic cross section through the nozzle 110a shown in FIG. 6. The nozzle is designed to prevent the camera from observing reflections within the stone into the bore of the nozzle which would naturally appear dark: if steps are not taken to address this then spurious dark features may appear on the diamond under inspection.

The nozzle 110a includes a wall 702 surrounding a bore 704 to which a vacuum is applied so as to suck a stone onto the nozzle. The wall 702 is formed from a clear material so as to allow light to pass through. The line of sight into the bore from the nozzle opening 708 is interrupted by an opaque partial obstruction 706, having a white diffusely reflecting underside. The obstruction is naturally illuminated by light passing from the surroundings through the transparent wall 702 of the nozzle so that appears to have approximately the same level of illumination as the other surroundings. An image obtained by the camera 228, viewing a stone along a path or ray that passes along the bore 704 of the nozzle 110a, will not include any spurious dark features introduced by the nozzle.

The obstruction 706 must be partial so as to allow communication between the nozzle opening 708 and the region of reduced pressure in the bore 704. The obstruction is therefore supported by discrete arms 710 extending from the wall 702 of the nozzle which are not visible in a direct line of sight up the nozzle. In FIG. 7 these arms are shown as extending laterally from the obstruction 710, but it will be appreciated that they could extend upwards from the obstruction so that they are effectively hidden behind the obstruction when looking into the nozzle. Any arrangement which will allow airflow around the obstruction through a labyrinth is likely to be suitable.

Figure 8:
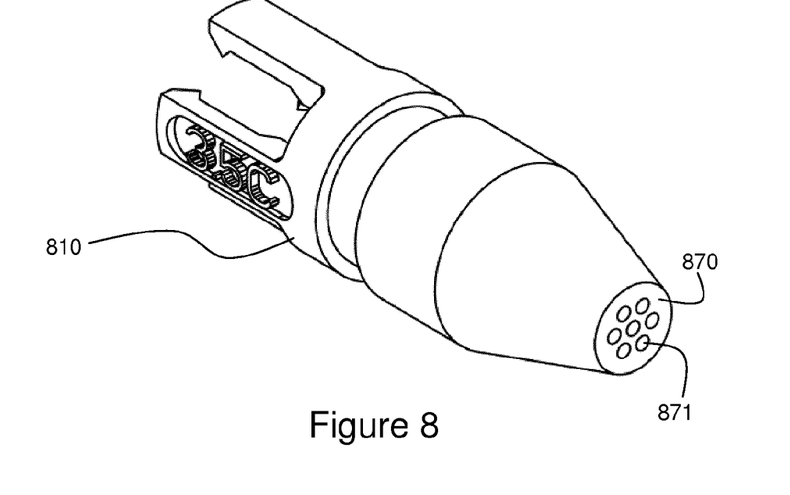
FIG. 8 is a view of an alternative nozzle.

FIG. 8 is a view of an alternative nozzle 810. It has been found that different mounting orientations of some stones caused a larger than desirable variance in measurement results. The measurement of stones picked up by the nozzle such that a point or corner is inserted into the mouth of the nozzle results in a much higher variance in measurement results than a mounting orientation with a flat face held against the nozzle aperture. In order to ensure that a stone is picked up with a flat face against the nozzle, a multi-bore nozzle 810 as shown in FIG. 8 may be used. In place of the single aperture 708 of the nozzle 110a shown in FIG. 7, the nozzle 810 has a generally flat bottom face 870 with a plurality of apertures 871 formed therethrough. In this example there are seven apertures—six arranged in a hexagon around a single central aperture—but it will be appreciated that other numbers and arrangements may be used. The effect of this is to force an orientation of a stone picked up by the nozzle that aligns a flat face with the apertures of the nozzle.

It will be appreciated that the nozzle may be provided with a single central bore leading to all of the apertures, or with a plurality of bores, each associated with its own aperture.

Other exemplary nozzles may be configured to permit measurements to be made through the nozzle. That is, measurement devices such as lasers, LEDs, spectrometers and cameras may be configured to emit and receive light through the nozzle instead of emitting and receiving light from locations adjacent the nozzle. One such exemplary nozzle is configured for use with measurement devices for detecting diamond containing material using Raman spectroscopy and comprising a light source arranged to emit light onto the stone, and a spectrometer arranged to receive luminescent light from the stone. The nozzle comprises a longitudinal bore and a bundle of optical fibres positioned within the bore. The bore is configured such that the air vacuum that runs up through the bore is diverted from the nozzle area in the lower section of the nozzle in order to make the bore available for locating the bundle of optical fibres therein. One of the bundle of optical fibres is arranged to receive light emitted by the light source and propagate the emitted light through an open end of the nozzle. The stone is held on the end of the nozzle by vacuum suction applied through the open end as explained above and is thereby exposed to the emitted light. Another of the bundle of optical fibres is arranged to receive luminescent light from the stone and propagate the luminescent light to the spectrometer. Using this nozzle design, diamond containing material may be detected through the nozzle while a stone is in transit on the nozzle to measurement locations used to obtain other measurements.

In an exemplary apparatus comprising such a nozzle design, the light source and the spectrometer rotate synchronously with the nozzle as the feeder hub rotates and are thereby able to determine whether the stone comprises diamond material while it is in transit on the nozzle. This provides the advantage that the Raman spectroscopy measurement may be undertaken over a longer period than in apparatuses in which the stone passes by a measurement device located at the side of the feeder hub.

In a further exemplary apparatus comprising the nozzle described above, an aperture is formed in the feeder hub and a light source and spectrometer are in a fixed position above the feeder hub. That is, the feeder hub is rotatable with respect to the light source and the spectrometer such that the aperture passes beneath them as the feeder hub rotates. In such apparatuses, as a stone is in transit on the nozzle past the aperture, light emitted from the light source is propagated through the aperture, through one of the optical fibres within the nozzle, through the open end of the nozzle and onto the stone located at the end of the nozzle. Luminescent light from the stone is received by another of the bundle of optical fibres and is propagated to the spectrometer.

The nozzle described above may also be used with other measurement devices.

Taking measurements through the nozzle allows a closer arrangement of the measurement device to the nozzle tip and stone. Further, if the height of the feeder hub is adjusted, the height of the measurement device would not need to be adjusted in a corresponding manner.

In one example, a machine is capable of sorting stones into different colour categories with an overall throughput of 8 stones per second and with stone having diameters ranging from about 1 mm to 7.5 mm.

The different colour categories are defined by a pre-programmed sort map. The sort map defines where the stones will ultimately end up. For example, it could be pre-programmed to sort three shades of yellow into one location or sort the same three shades of yellow into three separate locations.

If, for example, two or more stones are detected in a stone feed or the colour sort map cannot determine what category the stone should be on that run, they are recycled back into the hopper to start the journey again.

It will be appreciated that variations from the embodiments described above may still fall within the scope of the invention. For example, the array of nozzles has been described as attached to a circular feeder hub. However, arrangements can be envisaged in which the nozzles are driven by a belt drive rather than a solid hub. It can also be envisaged that in machine for taking complex measurements, a single robotic arm rather than an array of nozzles may be used. It will also be appreciated that the apparatus need not be used exclusively for sorting. For example, a series of measurements could be obtained for all the stones in a given parcel, but all of the stones may be dispensed into the same bin. The measurements obtained may then be used to assign a value to that parcel.

Furthermore, it will be appreciated that the apparatus can be used to inspect and/or sort both rough and cut gemstones.

The invention claimed is:

1. Apparatus for inspecting gemstones, comprising:
   a vacuum nozzle for picking up a gemstone from a supply of gemstones;
   a transport mechanism for transporting the nozzle and associated gemstone to one or more measurement locations;
   a measurement system comprising a plurality of measuring devices proximate to the one or more measurement locations, the measuring devices configured to measure one or more properties of the gemstone,
      wherein at least one of the plurality of measuring devices is located proximate to at least one of the one or more measurement locations in such a way as to measure at least one of the one or more properties of the gemstone while the gemstone is held on the nozzle,
      and wherein the transport mechanism is configured such that the gemstone is conveyed to the plurality of measuring devices in sequence, each receiving the gemstone at controlled times and locations;
   a control system operatively coupled to the vacuum nozzle and measurement system and configured so that the gemstone arrives at the or each measurement location at a time known by the measurement system; and
   a positive pressure application system for releasing the gemstone from the nozzle at an ejection location.

2. The apparatus of claim 1, further comprising nozzle manipulation means for changing the orientation of the gemstone as it travels between the measuring devices, optionally by rotating the nozzle about its own axis.

3. The apparatus of claim 1, wherein at least some of the measuring devices are substantially identical so as to measure the same property of the gemstone at different orientations.

4. The apparatus of claim 1, wherein the ejection location is coincident with one of the one or more measurement locations such that, following release from the nozzle, the gemstone falls along a predetermined path through the one or more measuring devices within a specified time window.

5. The apparatus of claim 1, further comprising a plurality of dispensing bins into which the gemstones can be dispensed, the bin into which each gemstone is dispensed being chosen in dependence on the one or more measured properties.

6. The apparatus of claim 5, comprising a plurality of ejection locations, each ejection location being associated with a delivery mechanism to one of the dispensing bins, the ejection location at which the positive pressure is applied for any given nozzle being chosen in dependence on the one or more measured properties of the stone held by that nozzle.

7. The apparatus of claim 5, further comprising:
a rotatable carousel comprising a plurality of socks and having at least a portion located beneath one of the one or more ejection locations so that a gemstone ejected at that ejection location falls into one of the socks;
a plurality of selectively actuable release points for releasing the gemstone from the socks, each release point associated with a delivery mechanism to one of the dispensing bins, the apparatus configured so that the activation of a release point is chosen in dependence on the measured properties of a stone carried by the sock passing through that release point.

8. The apparatus of claim 7, wherein the carousel is configured to rotate such that the sock passing under the ejection location is moving at substantially the same speed and in the same direction as the nozzle moving through the ejection location.

9. The apparatus of claim 7, further comprising a double feed detector for identifying if two or more stones are ejected at the ejection location into a single sock.

10. The apparatus of claim 1, wherein one of the measuring devices comprises a diffuse light source and an array of cameras at different locations and a means for rotating the nozzles between the different locations, the one of the measuring devices being coupled to a processing means for identifying a colour of the gemstone when illuminated by the light source.

11. The apparatus of claim 1, wherein one of the measuring devices comprises one or more of: a spectrometer for determining an absorption spectrum of a gemstone passing through that measurement cell; a collimated light source so as to obtain a number of silhouette images of each gemstone; and a diffuse light source and a camera located below the predetermined path for obtaining an image of each gemstone from beneath.

12. The apparatus of claim 11, further comprising processing means for constructing a 3D model of the shape of each gemstone from the series of images.

13. The apparatus of claim 1, wherein each nozzle comprises:
a wall surrounding a bore for supplying a vacuum to an opening of the nozzle, the wall being formed from a clear material;
an obstruction in the bore obstructing a line of sight from the opening into the bore, the partial obstruction including a diffuse reflecting surface on a side facing the opening; and
a support structure for holding the obstruction in place in such a way as to allow airflow around the obstruction.

14. An apparatus according to claim 1, wherein at least one nozzle comprises a wall surrounding a bore for supplying a vacuum to an opening of the nozzle, and wherein at least one measuring device is arranged to measure at least one optical property of the gemstone through the bore.

15. An apparatus according to claim 14, wherein the at least one nozzle further comprises at least one optical fibre within the bore and configured to allow airflow around the optical fibre.

16. An apparatus according to claim 14, wherein the at least one measuring device is synchronously movable with the at least one nozzle and arranged to allow measurement of the at least one optical property of the gemstone through the bore at any time during the transport of the nozzle and gemstone, or wherein the at least one measuring device is fixed with respect to the transport mechanism, and arranged to measure the at least one optical property of the gemstone through the bore as the gemstone passes a corresponding measurement location.

17. The apparatus of claim 1, further comprising an array of nozzles disposed around a rotatable hub configured to act as the transport mechanism.

18. The apparatus of claim 17, wherein the rotatable hub includes a series of apertures, each communicating with one of the nozzles, into which a jet of fluid is introducible in order to provide the application of positive pressure at that nozzle at the ejection location.

19. The apparatus of claim 17, further comprising a bowl for presenting the gemstones to the array of nozzles, the bowl rotatable in the same direction as the nozzle passing the pick-up location.

20. The apparatus of claim 19, wherein the bowl is laterally offset from the nozzle array, and wherein the bowl and nozzle array are configured to rotate in opposite directions.

21. The apparatus of claim 19, further comprising a cam surface located above the pick-up location, wherein each nozzle is located on a mount configured to follow the cam surface and move the nozzle closer to the bowl as that nozzle passes the pick-up location.

22. The apparatus of claim 19, wherein the nozzle array is configured to rotate around an axis at an angle compared to an axis of rotation of the bowl so that the nozzles approach the bowl as they approach the pick-up location.

23. The apparatus of claim 1, wherein the or each nozzle is provided with a plurality of apertures formed through a generally flat face so as to increase the likelihood of a flat face of the stone being held against the nozzle.

24. A method for sorting gemstones, comprising:
picking up gemstones individually from a supply of gemstones using a moving nozzle or array of nozzles under vacuum;
performing one or more measurements on each gemstone while mounted on its associated nozzle to identify at least one property of that gemstone;
releasing each gemstone into a bin selected from a plurality of bins in dependence on the measured property of that gemstone.

25. A method for sorting gemstones, comprising:
picking up gemstones individually from a supply of gemstones using a moving nozzle or array of nozzles under vacuum;
performing one or more measurements on each gemstone while mounted on its associated nozzle to identify at least one property of that gemstone,
releasing the gemstone at an ejection location so that it passes in freefall through a measurement cell; and
measuring at least one property of a gemstone in freefall through the measurement cell.

26. A nozzle for supporting a gemstone, comprising:
a wall surrounding a bore for supplying a vacuum to an opening of the nozzle, the wall being formed from a clear material;
an obstruction in the bore obstructing a line of sight from the opening into the bore, the partial obstruction including a diffuse reflecting surface on a side facing the opening; and
a support structure for holding the obstruction in place in such a way as to allow airflow around the obstruction.

27. A nozzle for supporting a gemstone, comprising a central bore for supplying a vacuum to a plurality of apertures formed through a generally flat support face at the end of the nozzle against which a flat face of the gemstone can be held.

* * * * *